United States Patent [19]

Marhold et al.

[11] Patent Number: 5,493,048
[45] Date of Patent: Feb. 20, 1996

[54] FLUORO-TRIFLUOROMETHYLBENZOIC ACID DERIVATIVES

[75] Inventors: Albrecht Marhold, Leverkusen; Peter Andres, Leichlingen, both of Germany

[73] Assignee: Bayer Aktiengesellschaft, Leverkusen, Germany

[21] Appl. No.: 180,590

[22] Filed: Jan. 12, 1994

[30] Foreign Application Priority Data

Jan. 19, 1993 [DE] Germany .................. 43 01 245.0

[51] Int. Cl.$^6$ .................................. C07C 69/76
[52] U.S. Cl. ................. 560/103; 562/424; 562/493; 562/840
[58] Field of Search ................. 560/103; 562/424, 562/493, 840

[56] References Cited

U.S. PATENT DOCUMENTS 3,985,799  10/1976  Houlihan ..................... 260/515 A
5,194,628   3/1993  Ackermann et al. ............ 548/526

FOREIGN PATENT DOCUMENTS 0302525  2/1989  European Pat. Off. .

OTHER PUBLICATIONS

CA 113:190951 1990.
M. Schlosser; Synlett 1990, 747.
M. Schlosser; Synlett 1991, 119.
S. Sugawara, N. Ishikawa; J. Chem. Soc. Jap. Ind. Chem. Sect. 73 (1970) 972–979.

Primary Examiner—Paul J. Killos
Attorney, Agent, or Firm—Sprung Horn Kramer & Woods

[57] ABSTRACT

The new fluoro-trifluoromethylbenzoic acid derivatives of the general formula (I)

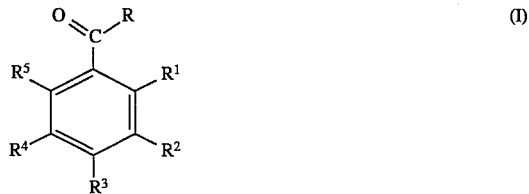

wherein the substituents R, $R^1$, $R^2$, $R^3$, $R^4$ and $R^5$ have the meaning given in the description, are suitable as starting substances for the preparation of antibacterial agents and feed additives.

6 Claims, No Drawings

FLUORO-TRIFLUOROMETHYLBENZOIC ACID DERIVATIVES

The present invention relates to new fluoro-trifluoromethylbenzoic acid derivatives, new intermediate products and processes for their preparation.

The new fluoro-trifluoromethylbenzoic acid derivatives correspond to the general formula (I)

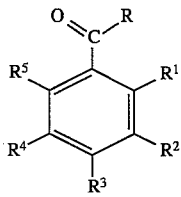
(I)

wherein

R represents hydroxyl, —OM, halogen or $C_1$–$C_4$-alkoxy, wherein

M represents an alkali metal, preferably lithium, sodium or potassium, and either a) $R^1$ represents F, $R^2$ represents F, $R^3$ represents H, $R^4$ represents H and $R^5$ represents $CF_3$ or b) $R^1$ represents F, $R^2$ represents $CF_3$, $R^3$ represents F, $R^4$ represents H and $R^5$ represents H or c) $R^1$ represents F, $R^2$ represents $CF_3$, $R^3$ represents H, $R^4$ represents H and $R^5$ represents F or d) $R^1$ represents F, $R^2$ represents F, $R^3$ represents $CF_3$, $R^4$ represents H and $R^5$ represents H or e) $R^1$ represents F, $R^2$ represents H, $R^3$ represents $CF_3$, $R^4$ represents H and $R^5$ represents F or f) $R^1$ represents F, $R^2$ represents F, $R^3$ represents F, $R^4$ represents H and $R^5$ represents $CF_3$ or g) $R^1$ represents F, $R^2$ represents $CF_3$, $R^3$ represents F, $R^4$ represents H and $R^5$ represents F or h) $R^1$ represents F, $R^2$ represents F, $R^3$ represents H, $R^4$ represents $CF_3$ and $R^5$ represents F or i) $R^1$ represents F, $R^2$ represents F, $R^3$ represents F, $R^4$ represents $CF_3$ and $R^5$ represents H or k) $R^1$ represents F, $R^2$ represents F, $R^3$ represents $CF_3$, $R^4$ represents F and $R^5$ represents H or l) $R^1$ represents F, $R^2$ represents F, $R^3$ represents $CF_3$, $R^4$ represents H and $R^5$ represents F.

The new fluoro-trifluoromethylbenzoic acid derivatives of the formula (I) where R=hydroxyl can be prepared in a manner which is known per se (compare, for example, M. Schlosser, Synlett 1990, 747) by reaction of metallized fluoro-trifluoromethylbenzene derivatives of the formula (II)

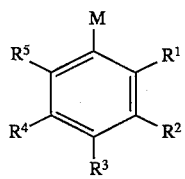
(II)

wherein

M represents an alkali metal, preferably lithium, sodium or potassium, and either a) $R^1$ represents F, $R^2$ represents F, $R^3$ represents H, $R^4$ represents H and $R^5$ represents $CF_3$ or b) $R^1$ represents F, $R^2$ represents $CF_3$, $R^3$ represents F, $R^4$ represents H and $R^5$ represents H or c) $R^1$ represents F, $R^2$ represents $CF_3$, $R^3$ represents H, $R^4$ represents H and $R^5$ represents F or d) $R^1$ represents F, $R^2$ represents F, $R^3$ represents $CF_3$, $R^4$ represents H and $R^5$ represents H or e) $R^1$ represents F, $R^2$ represents H, $R^3$ represents $CF_3$, $R^4$ represents H and $R^5$ represents F or f) $R^1$ represents F, $R^2$ represents F, $R^3$ represents F, $R^4$ represents H and $R^5$ represents $CF_3$ or g) $R^1$ represents F, $R^2$ represents $CF_3$, $R^3$ represents F, $R^4$ represents H and $R^5$ represents F or h) $R^1$ represents F, $R^2$ represents F, $R^3$ represents H, $R^4$ represents $CF^3$ and $R^5$ represents F or i) $R^1$ represents F, $R^2$ represents F, $R^3$ represents F, $R^4$ represents $CF_3$ and $R^5$ represents H or k) $R^1$ represents F, $R^2$ represents F, $R^3$ represents $CF_3$, $R^4$ represents F and $R^5$ represents H or l) $R^1$ represents F, $R^2$ represents F, $R^3$ represents $CF_3$, $R^4$ represents H and $R^5$ represents F, with carbon dioxide, if appropriate in the presence of a diluent, at a temperature of −150° to 50°, preferably of −80° to 30° C. and subsequent reaction of the alkali metal carbonates of the formula (I) formed, where R=OM, with an acid, such as, for example, hydrochloric acid.

The new fluoro-trifluoromethylbenzoic acid derivatives of the formula (I) wherein R represents halogen can be prepared in a manner which is known per se by a procedure in which compounds of the formula (I) wherein R represents hydroxyl or —OM are reacted with a halogenating agent, such as, for example, a sulphur or phosphorus halide, if appropriate in the presence of a diluent, at a temperature of 0° to 160° C., preferably of 60° to 120° C.

The new compounds of the formula (I) wherein R represents $C_1$–$C_4$-alkoxy can be prepared in a manner which is known per se by a procedure in which compounds of the formula (I) wherein R represents hydroxyl or halogen are reacted with an alcohol of the formula (III)

$$R^6\text{—OH} \qquad (III)$$

wherein $R^6$ represents $C_1$–$C_4$-alkyl, if appropriate in the presence of a diluent and if appropriate in the presence of an acid-binding agent, at a temperature of 20° to 160° C., preferably of 50° to 120° C.

The metallized compounds of the formula (II) are new and the present invention likewise relates to them.

The metallized compounds of the formula (II) can be prepared in a manner which is known per se (compare, for example, M. Schlosser, Synlett 1990, 747), by a procedure in which fluoro-trifluoromethylbenzenes of the formula (IV)

(IV)

wherein $R^1$ to $R^5$ have the meaning already given above for formula (I), are reacted with an alkyl metallate, such as, for example, methyllithium, n-butyllithium, -sodium or -potassium or tert-butyllithium, -sodium or -potassium, preferably with n-butyllithium, if appropriate in the presence of a diluent, at a temperature of −150° to 30°, preferably of °100° to −20° C. The compounds of the formula (IV) are generally known compounds in organic chemistry.

The metallized fluoro-trifluoromethylbenzene derivatives (II) are preferably further reacted directly, without intermediate isolation, with the compounds (I) according to the invention where R=hydroxyl.

If, for example, 1,3-difluoro-2-trifluoromethylbenzene lithiumized in the 6-position is used as the starting compound, this is reacted with carbon dioxide and the product is then hydrolysed with hydrochloric acid, the process according to the invention for the preparation of the compounds (I) where R=hydroxyl can be represented by the following equation:

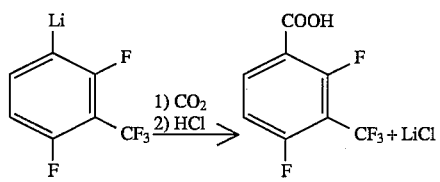

The reaction of the metallized fluoro-trifluorobenzene derivatives can be carried out either with gaseous or with solid carbon dioxide. The gaseous carbon dioxide is preferably introduced into the reaction solution under atmospheric pressure.

The process according to the invention for the preparation of compounds (I) where R=hydroxyl is preferably carried out in the presence of a diluent. In principle, the following diluents are suitable here: lower hydrocarbons, ethers or mixtures of the two.

Pentane, hexane, heptane, diethyl ether or tetrahydrofuran is preferably used as the diluent.

The temperature can be varied within a wide range in the process according to the invention for the preparation of the compounds (I) where R=hydroxyl. In general, the process is carried out at a temperature of −150° to 50° C., preferably of −80° to 30° C.

To carry out the process according to the invention for the preparation of the compounds (I) where R=hydroxyl, a procedure is expediently followed in which gaseous $CO_2$ in an amount of 0.9 to 10 mol, preferably 2.0 to 6.0 mol of $CO_2$ per mol of compound (II), is passed into a solution of the compound (II) in a mixture of tetrahydrofuran (THF), diethyl ether and hexane at a temperature of −80° to −20° C.

Hydrolysis is then carried out with 1 to 1.5 equivalents of hydrochloric acid. Working up is carried out by extraction under aqueous conditions, for example, by separation of the phases, extraction with diethyl ether, subsequent washing with hydrochloric acid and water and drying of the organic phase over sodium sulphate and concentration.

If, for example, 2,4-difluoro-3-trifluoromethylbenzoic acid is used as the starting compound and this is reacted with thionyl chloride, the process according to the invention for the preparation of the compounds (I) where R=halogen can be represented by the following equation:

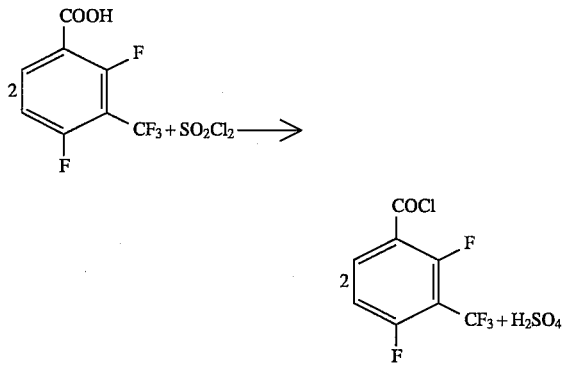

The process according to the invention for the preparation of the compounds (I) where R=halogen is preferably carried out without addition of a diluent.

The temperature can be varied within a wide range for the preparation of the compounds (I) where R=halogen by the process according to the invention. In general, the preparation is carried out at a temperature of 0° to 160° C., preferably of 60° to 20° C.

For carrying out the process according to the invention for the preparation of the compounds (I) where R=halogen, a procedure is in general followed in which the compound (I) where R=hydroxyl is initially introduced into the reaction vessel and the halogenating agent, for example thionyl chloride, is added dropwise, with exclusion of moisture and at a temperature of preferably 0° C., in an amount of 1–3 mol, preferably 2 mol per mol of compound (I) where R=OH. The mixture is then stirred under reflux (60°–120° C.) until the evolution of HCl has ended, excess $SOCl_2$ is distilled off and the product is then distilled.

If, for example, 2,4-difluoro-3-trifluoromethylbenzoic acid and methanol are used as starting compounds, the process according to the invention for the preparation of the compounds (I) where R=$C_1$–$C_4$-alkoxy can be represented by the following equation:

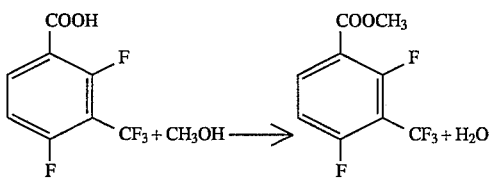

The process according to the invention for the preparation of the compounds (I) where R=$C_1$–$C_4$-alkoxy is preferably carried out in the absence of a diluent. However, in principle, lower chlorinated hydrocarbons are possible diluents, chloroform being preferred.

The temperature can be varied within a wide range in carrying out the process according to the invention for the preparation of the compounds (I) where R=$C_1$–$C_4$-alkoxy. In general, the process is carried out at temperatures of 20° to 160° C., preferably of 50° to 120° C.

For carrying out the process according to the invention for the preparation of the compounds (I) where R=$C_1$–$C_4$-alkoxy, a procedure is in general followed in which a mixture of 1 mol of the compound (I) where R=hydroxyl and 5 mol of the alcohol of the formula (III) is initially introduced into the reaction vessel, 0.2 ml of concentrated sulphuric acid is added and the mixture is stirred under reflux and with exclusion of moisture for 5 hours. Most of the excess alcohol is then distilled off and the residue is worked up by extraction under aqueous conditions. The ester can be distilled for purification.

If, for example, 2,4-difluoro-3-trifluoromethylbenzoyl chloride and methanol are used as starting compounds, the process according to the invention for the preparation of the compounds (I) where R=$C_1$–$C_4$-alkoxy can be represented by the following equation:

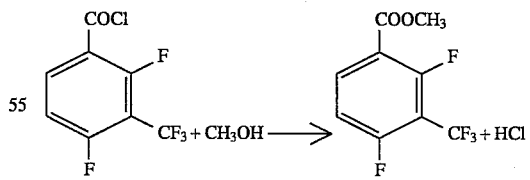

The process according to the invention for the preparation of the compounds (I) where R=$C_1$–$C_4$-alkoxy is carried out either without addition of a diluent or in the presence of a diluent, possible diluents being in principle ether and chlorinated lower hydrocarbons.

A preferred diluent is diethyl ether.

The process according to the invention for the preparation of the compounds (I) where R=$C_1$–$C_4$-alkoxy is carried out, if appropriate, in the presence of an acidbinding agent.

Possible acid-binding agents are, for example, tertiary amines, such as triethylamine.

For carrying out the process according to the invention for the preparation of the compounds (I) where R=$C_1$-$C_4$-alkoxy, a procedure is in general followed in which the compound (I) where R=halogen is first dissolved in ether and the alcohol of the formula (III) is added dropwise, in an amount of 1 mol per mol, to this solution in the presence of $NEt_3$ as the acid-binding agent at a temperature of preferably 20°–50° C. The solid is then filtered off with suction, the filtrate is worked up by extraction under aqueous conditions and, if appropriate, the product is isolated by distillation.

If, for example, 1,3-difluoro-2-trifluoromethylbenzene and n-butyllithium are used as starting compounds, the process according to the invention for the preparation of the compounds of the formula (II) can be represented by the following equation:

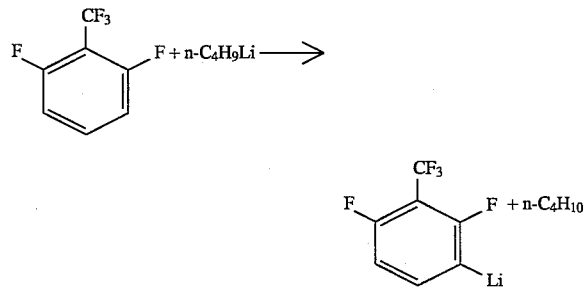

The process according to the invention for the preparation of the compounds (II) is preferably carried out in the presence of a diluent. In principle, possible diluents here are: lower hydrocarbons, ethers or mixtures of the two.

Diethyl ether, tetrahydrofuran, hexane or mixtures thereof are preferably used.

The process according to the invention for the preparation of the compounds (II) is in general carried out at temperatures of –150° to 30° C. preferably of –100° to –20° C., particularly preferably –80° to –50° C.

The process according to the invention for the preparation of the compounds (II) is preferably carried out under an inert gas atmosphere, possible inert gases being, for example, argon or nitrogen.

Preferably, the preparation of the compounds (II) is carried out by a procedure in which the fluoro-trifluoromethylbenzene of the formula (IV) is dissolved in a 1:1 mixture of THF and $Et_2O$, and the organometallic compound, dissolved in hexane, is added dropwise to this solution under an inert gas atmosphere at a temperature of preferably –80° to –30° C.

The compounds of the formula (II) can be isolated by removal of the solvent (distillation).

The fluoro-trifluoromethylbenzoic acid derivatives of the formula (I) can be used, for example, for the preparation of antibacterial agents and feed additives.

Thus, for example, 1) 2,4-difluoro-3-trifluoromethylbenzoic acid can be converted, by reaction with a halogenating agent, such as thionyl chloride, into 2,4-difluoromethylbenzoyl chloride, which 2) is reacted with diethyl malonate to give diethyl (2,4-difluoro-3-trifluoromethylbenzoyl)-malonate, subsequently 3) the compound obtained according to step 2) is converted, by hydrolysis and decarboxylation, into ethyl (2,4-difluoro-3-trifluoromethylbenzoyl)acetate, which 4) is converted, by reaction with ethyl orthoformate, into ethyl 3-ethoxy-2-(2,4-difluoro-3-trifluoro-methylbenzoyl)acrylate, 5) the compound obtained according to step 4) is reacted with cyclopropylamine to give ethyl 3-cyclopropylamino-2-(2,4-difluoro-4-trifluoromethyl-benzoyl)acrylate, 6) the compound obtained according to step 5) is converted, by splitting off of HF, into the corresponding quinolonecarboxylic acid ester derivative which 7) is converted by hydrolysis into the corresponding quinolonecarboxylic acid derivative.

Further quinolonecarboxylic acid derivatives can be prepared from the compounds of the formula (I) according to the invention in a corresponding manner.

The reaction sequence described above can be represented by way of example by the following equation:

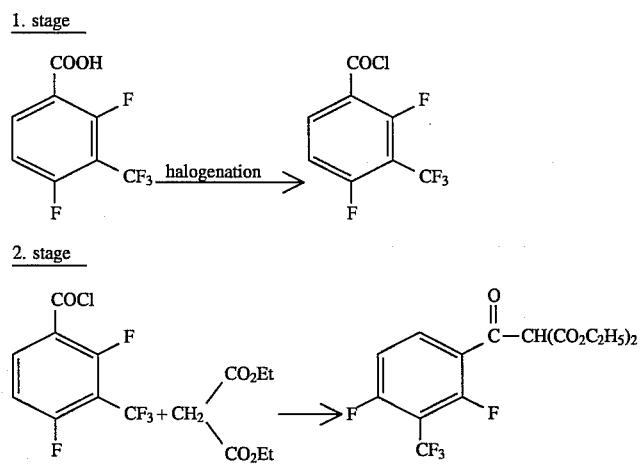

3. stage

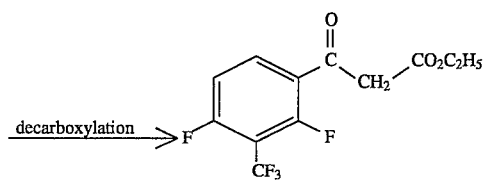

4. stage

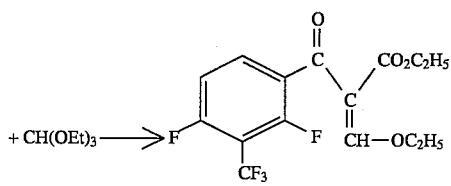

5. stage

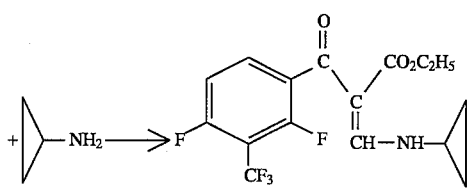

6. stage

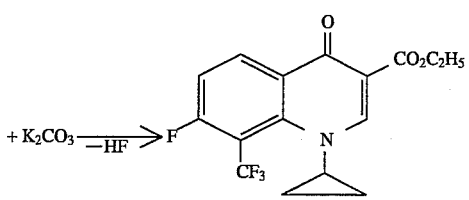

7. stage

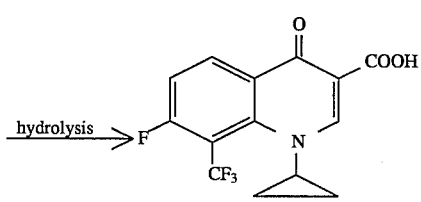

The quinolonecarboxylic acid derivatives obtained in stage 7) correspond to the general formula (V)

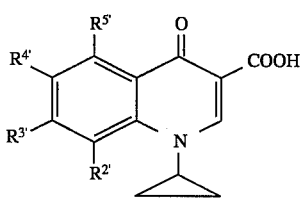 (V)

wherein
either
n) $R^{2'}$ represents $CF_3$ and $R^{3'}$ represents F and $R^{4'}$ represents H and $R^{5'}$ represents H or
o) $R^{2'}$ represents F and $R^{3'}$ represents F and $R^{4'}$ represents H and $R^{5'}$ represents $CF_3$ or
p) $R^{2'}$ represents $CF_3$ and $R^{3'}$ represents F and $R^{4'}$ represents H and $R^{5'}$ represents F.

The quinolonecarboxylic acid derivatives of the formula (V) can be converted, by reactions with compounds of the formula (VI)

$$Z-H \quad \quad (VI)$$

in which
Z represents radicals having the structures

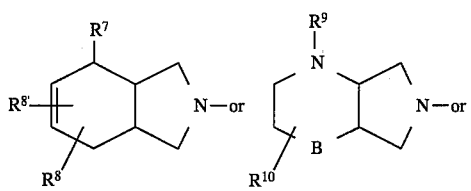

wherein
R⁷ represents hydrogen, hydroxyl, —NR¹¹R¹², hydroxymethyl or —CH₂—NR¹¹R¹²,
wherein
R¹¹ denotes hydrogen, optionally hydroxyl-substituted $C_1$-$C_3$-alkyl, alkoxycarbonyl having 1 to 4 C atoms in the alkoxy part or $C_1$-$C_3$-acyl and
R¹² denotes hydrogen or methyl,
R⁸ represents hydrogen, straight-chain or branched $C_1$-$C_3$-alkyl or cyclopropyl,
R⁸' represents hydrogen or methyl,
R⁹ represents hydrogen or methyl,
R¹⁰ represents hydrogen, methyl or radicals having the structures —CH=CH—CO₂R⁹', —CH₂—CH₂—CO₂R⁹', —CH₂—CO—CH₃ or —CH₂—CN,
R⁹' represents methyl or ethyl and
B represents —CH₂—, O or a direct bond,
into quinolonecarboxylic acid derivatives of the formula (VII)

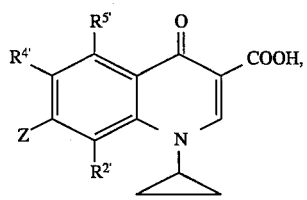

wherein
R²', R⁴', R⁵', R⁷ and Z have the abovementioned meaning.

PREPARATION EXAMPLES

EXAMPLE 1 a) 1,3-Difluoro-6-lithio-2-trifluoromethylbenzene

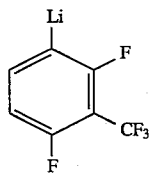

Under a nitrogen atmosphere, 0.5 mol of 1,3-di fluoro-2-trifluoromethylbenzene is dissolved in a mixture of 300 ml of absolute tetrahydrofuran and 300 ml of absolute diethyl ether, 220 ml (0.55 mol) of a 2.5 molar solution of n-butyllithium in hexane are added dropwise at –70° C. and the mixture is stirred for one hour.

b) 2,4-Difluoro-3-trifluoromethylbenzoic acid

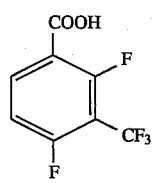

The 1,3-difluoro-6-lithio-2-trifluoromethylbenzene formed is converted into 2,4-difluoro-3-trifluoromethylbenzoic acid with intermediate isolation. For this, 200 g of carbon dioxide are passed, at –70° C., into the solution obtained according to 1a).

The mixture is then allowed to fall to 5° C. and is subsequently stirred for 1 hour and hydrolysed with 200 ml of 2N hydrochloric acid. The aqueous phase is separated off and extracted twice with diethyl ether. The combined organic phases are washed with dilute hydrochloric acid and with water, dried over magnesium sulphate and concentrated.

98 g of 2,4-difluoro-3-trifluoromethylbenzoic acid of melting point 108°110° C. are obtained, corresponding to a yield of 86%.

The fluoro-trifluoromethylcarboxylic acids shown in Table 1 were obtained analogously to Example 1b) from the corresponding lithiumized compounds.

TABLE 1

| Example No. | Compound | M.p. [°C.] | B.p. [°C.] (p[mbar]) | Yield [%] |
|---|---|---|---|---|
| 2 | ![F,COOH,F₃C,F] | 76–78 | 127–129 (22) | 92 |
| 3 | ![F,COOH,F₃C,F] | 112 | | 84 |
| 4 | ![CF₃,COOH,F,F] | 83–84 | 106–108 (0.3) | 89 |
| 5 | ![F,COOH,F,CF₃] | 70–71 | 85–87 (0.3) | 43 |
| 6 | ![CF₃,COOH,F,F,F] | 86–87 | 101–103 (0.3) | 75 |

EXAMPLE 7

2,4-Difluoro-3-trifluoromethylbenzoyl chloride

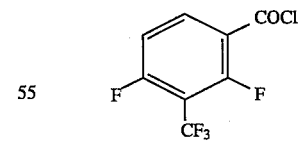

19.3 g (0.085 mol) of 2,4-difluoro-3-trifluoromethylbenzoic acid according to Example 1b) are introduced in portions into 130 ml of thionyl chloride at room temperature. When the metering has ended, the mixture is heated at 80° C. until the evolution of gas has ended. The excess thionyl chloride is then separated off by distillation and the product is further reacted directly.

Yield: 20.0 g (90% of theory)

EXAMPLE 8

2,4,6-Trifluoro-3-trifluoromethylbenzoyl chloride

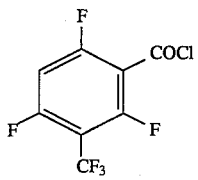

5.8 g (0.024 mol) of 2,4,6-trifluoro-3-trifluoromethylbenzoic acid according to Example 5 are introduced in portions into 40 ml of thionyl chloride at room temperature. When the metering has ended, the mixture is heated at 80° C. until the evolution of gas has ended. Thereafter, the excess thionyl chloride is separated off by distillation and the crude product is further reacted directly.

Yield: 6.0 g (95% of theory)

EXAMPLE 9

2,3,4-Trifluoro-6-trifluoromethylbenzoyl chloride

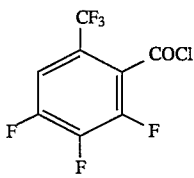

5.8 g (0.024 mol) of 2,3,4-trifluoro-6-trifluoromethylbenzoic acid according to Example 4 are introduced in portions into 40 ml of thionyl chloride at room temperature. When the metering has ended, the mixture is heated at 80° C. until the evolution of gas has ended. The excess thionyl chloride is then separated off by distillation and the crude product is further reacted directly.

Yield: 5.0 g (79% of theory)

EXAMPLE 10

1-Cyclopropyl-7-fluoro-8-trifluoromethyl-1,4-dihydro-4-oxo-3-quinolinecarboxylic acid

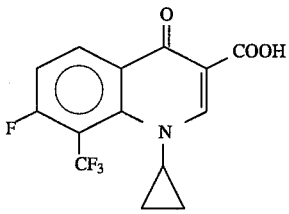

a) Diethyl (2,4-difluoro-3-trifluoromethylbenzoyl)malonate 2.15 g (0.09 mol) of magnesium filings are initially introduced into 4.8 ml of ethanol, the reaction is started with a few drops of carbon tetrachloride and a solution of 12.8 g (0.075 mol) of diethyl malonate in 9 ml of ethanol and 35 ml of toluene is then added dropwise such that the internal temperature is between 50° and 60° C. The mixture is then subsequently stirred at 60° C. for one hour. A solution of 20.0 g (0.082 mol) of 2,4-difluoro-3-trifluoromethylbenzoyl chloride according to Example 7 in 9 ml of toluene is added dropwise at −10° to −5° C. and the mixture is subsequently stirred at 0° C. for one hour and then by warming to room temperature. It is poured onto 35 ml of ice-water, 5.7 ml of concentrated sulphuric acid are added and the mixture is extracted with toluene. The organic phase is washed with saturated sodium chloride solution and the solvent is removed in vacuo.

Crude yield: 30.0 g b) Ethyl (2,4-difluoro-3-trifluoromethylbenzoyl)acetate 30.0 g of the crude product obtained in a) are heated under reflux in 30 ml of water with 0.96 g of p-toluenesulphonic acid for 4.5 hours. The cooled mixture is extracted with methylene chloride and the organic phase is washed with saturated sodium chloride solution, dried over sodium sulphate and concentrated in vacuo.

Crude yield: 22 g c) Ethyl 3-ethoxy-2-(2,4-difluoro-3-trifluoromethylbenzoyl)acrylate 22 g of the product obtained under b) are heated at 150°–160° C. with 17.4 g (0.12 mol) of ethyl orthoformate and 19.4 g (0.19 mol) of acetic anhydride for two hours. Excess reagent is removed first in vacuo and then under a high vacuum up to a bath temperature of 100° C.

Crude yield: 23.1 g d) Ethyl 3-cyclopropylamino-2-(2,4-difluoro-4-trifluoromethylbenzoyl)-acrylate 23.0 g (0.065 mol) of the product obtained under c) are initially introduced into 140 ml of ethanol at 0° C. and 4.08 g (0.072 mol) of cyclopropylamine are added dropwise. The mixture is subsequently stirred at room temperature overnight, 140 ml of water are added dropwise and the product which has precipitated out is isolated. It is rinsed with water and dried at about 100° C.

Yield: 9.4 g (39% of theory) Melting point: 104°–105° C.

e) Ethyl 1-cyclopropyl-7-fluoro-8-trifluoromethyl-1,4-dihydro-4-oxo-3-quinolinecarboxylate 9.0 g (0.025 mol) of the product obtained under d) are heated at 100° C. with 3.9 g (0.028 mol) of potassium carbonate in 50 ml of dimethylformamide for four hours. The cooled mixture is poured onto icewater and the product is isolated, rinsed with water and dried at 100° C.

Yield: 8.1 g (98% of theory) Melting point: 154°–155° C.

f) 1-Cyclopropyl-7-fluoro-8-trifluoromethyl-1,4-dihydro-4-oxo-3-quinolinecarboxylic acid 8.0 g (0.023 mol) of the product obtained under e) are heated at 140° C. in a mixture of 30 ml of acetic acid, 30 ml of water and 3 ml of concentrated sulphuric acid for two hours. The cooled mixture is poured onto ice-water and the product which has precipitated is isolated, rinsed with water and dried at 100° C.

Yield: 7.0 g (96% of theory) Melting point: 209°–210° C.

EXAMPLE 11

1-Cyclopropyl-5,7-difluoro-8-trifluoromethyl-1,4-dihydro-4-oxo-3-quinolinecarboxylic acid

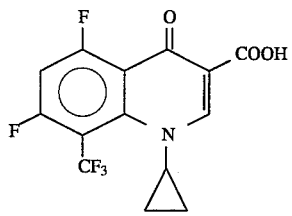

Diethyl (2,4,6-trifluoro-3-trifluoromethylbenzoyl)malonate 0.58 g (0.024 mol) of magnesium filings is initially introduced into 1.3 ml of ethanol, the reaction is started with a few drops of carbon tetrachloride and a solution of 3.4 g (0.019 mol) of diethyl malonate in 2.4 ml of ethanol and 9 ml of toluene is then added dropwise such that the internal temperature is between 50° and 60° C. The mixture is then subsequently stirred at 60° C. for one hour. A solution of 5.8 g (0.027 mol) of 2,4,6-trifluoro-3-trifluoromethylbenzoyl chloride according to Example 8 in 2.5 ml of toluene is added dropwise at −10° to −5° C. and the mixture is subsequently stirred at 0° C. for one hour and then while warming to room temperature. It is poured onto 10 ml of ice-water, 1.5 ml of concentrated sulphuric acid are added and the mixture is extracted with toluene. The organic phase is washed with saturated sodium chloride solution and the solvent is removed in vacuo.

Crude yield: 8.6 g b) Ethyl (2,4,6-trifluoro-3-trifluoromethylbenzoyl)acetate 8.6 g of the crude product obtained in a) are heated under reflux in 9 ml of water with 0.26 g of p-toluenesulphonic acid for 4.5 hours. The cooled mixture is extracted with methylene chloride and the organic phase is washed with saturated sodium chloride solution, dried over sodium sulphate and concentrated in vacuo.

Crude yield: 5.6 g c) Ethyl 3-ethoxy-2-(2,4,6-trifluoro-3-trifluoromethylbenzoyl)acrylate 5.4 g (0.017 mol) of the product obtained under b) are heated at 150°–160° C. with 4.0 g (0.027 mol) of ethyl orthoformate and 4.45 g (0.043 mol) of acetic anhydride for two hours. Excess reagent is removed first in vacuo and then under a high vacuum up to a bath temperature of 100° C.

Crude yield: 3.8 g d) Ethyl 3-cyclopropylamino-2-(2,4,6-trifluoro-4-trifluoromethylbenzoyl)acrylate 3.8 g (0.01 mol) of the product obtained under c) are initially introduced into 22 ml of ethanol at 0° C. and 0.63 g (0.011 mol) of cyclopropylamine is added dropwise. The mixture is subsequently stirred overnight at room temperature, 22 ml of water are added dropwise and the product which has precipitated is isolated. It is rinsed with water and dried at about 100° C.

Yield: 3.3 g (86% of theory) Melting point: 146°–148° C.

e) Ethyl 1-cyclopropyl-5,7-difluoro-8-trifluoromethyl 1,4-dihydro-4-oxo-3-quinolinecarboxylate 3.5 g (9.2 mmol) of the product obtained under d) are heated at 100° C. with 1.45 g (0.01 mol) of potassium carbonate in 18 ml of dimethylformamide for one hour. The cooled mixture is poured onto ice-water and the product is isolated and rinsed with water. The product is purified over silica gel using the mobile phase cyclohexane/tetrahydrofuran 7/3.

Yield: 1.4 g (42% of theory) Melting point: 197°–198° C.

f) 1-Cyclopropyl-5,7-difluoro-8-trifluoromethyl-1,4-dihydro-4-oxo-3-quinolinecarboxylic acid 1.4 g (3.9 mmol) of the product obtained under e) are heated at 140° C. in a mixture of 5 ml of acetic acid, 5 ml of water and 0.5 ml of concentrated sulphuric acid for two hours. The cooled mixture is poured onto ice-water and the product which has precipitated is isolated, rinsed with water and dried at 100° C.

Yield: 1.1 g (84% of theory) Melting point: 208°–210° C.

EXAMPLE 12

1-Cyclopropyl-7,8-difluoro-5-trifluoromethyl-1,4-dihydro-4-oxo-3-quinolinecarboxylic acid

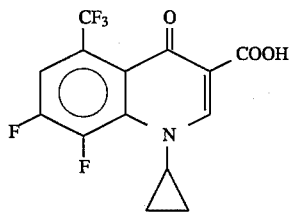

a) Diethyl (2,3,4-trifluoro-6-trifluoromethylbenzoyl)malonate 0.47 g (0.019 mol) of magnesium filings is initially introduced into 1.0 ml of ethanol, the reaction is started with a few drops of carbon tetrachloride and a solution of 2.8 g (0.016 mol) of diethyl malonate in 2.0 ml of ethanol and 7.5 ml of toluene is then added dropwise such that the internal temperature is between 50° and 60° C. The mixture is then subsequently stirred at 60° C. for one hour. A solution of 4.8 g (0.027 mol) of 2,3,4-trifluoro-6-trifluoromethylbenzoyl chloride according to Example 9 in 2.0 ml of toluene is added dropwise at −10° to −5° C. and the mixture is subsequently stirred at 0° C. for one hour and then while warming to room temperature. It is poured onto 10 ml of ice-water, 1.25 ml of concentrated hydrochloric acid are added and the mixture is extracted with toluene. The organic phase is washed with saturated sodium chloride solution and the solvent is removed in vacuo.

Crude yield: 6.6 g b) Ethyl (2,3,4-trifluoro-6-trifluoromethylbenzoyl)acetate 6.6 g of the crude product obtained in a) are heated under reflux in 7.5 ml of water with 0.21 g of p-toluenesulphonic acid for 4.5 hours. The cooled mixture is extracted with methylene chloride and the organic phase is washed with saturated sodium chloride solution, dried over sodium sulphate and concentrated in vacuo.

Crude yield: 4.2 g c) Ethyl 3-Ethoxy-2-(2,3,4-trifluoro-6-trifluoromethylbenzoyl)acrylate 4.0 g (0.013 mol) of the product obtained under b) are heated at 150°–160° C. with 3.5 g (0.024 mol) of ethyl orthoformate and 3.4 g (0.033 mol) of acetic anhydride for two hours. Excess reagent is removed first in vacuo and then under a high vacuum up to a bath temperature of 100° C.

Crude yield: 2.7 g d) Ethyl 3-cyclopropylamino-2-(2,3,4-trifluoro-6-trifluoromethylbenzoyl)acrylate 2.7 g (7.3 mmol) of the product obtained under c) are initially introduced into 16 ml of ethanol at 0° C. and 0.46 g (8 mmol) of cyclopropylamine is added dropwise. The mixture is subsequently stirred overnight at room temperature, 16 ml of water are added dropwise and the product which has precipitated is isolated. It is rinsed with water and dried at about 100° C.

Yield: 2.1 g (75% of theory) Melting point: 165°–168° C.

e) Ethyl 1-cyclopropyl-7,8-difluoro-5-trifluoromethyl-1,4-dihydro-4-oxo-3-quinolinecarboxylate 2.1 g (5.5 mmol) of tile product obtained under d) are heated at 100° C. with 0.88 g (6.4 mmol) of potassium carbonate in 11 ml of dimethylformamide for one hour. The cooled mixture is poured onto icewater and the product is isolated and rinsed with water.

Yield: 1.7 g (85% of theory) Melting point: 188°–190° C.

f) 1-cyclopropyl-5,7-difluoro-8-trifluoromethyl-1,4-dihydro-4-oxo-3-quinolinecarboxylic acid 1.5 g (4.2 mmol) of the product obtained under e) are heated at 140° C. in a mixture of 5.5 ml of acetic acid, 5.5 ml of water and 0.55 ml of concentrated sulphuric acid for two hours. The cooled mixture is poured onto ice-water and the product which has precipitated is isolated, rinsed with water and dried at 100° C.

Yield: 1.3 g (92% of theory) Melting point: 226°–228° C.

EXAMPLE 13

7-(4-Amino-1,3,3a,4,7,7a-hexahydroisoindol-2-yl)-1cyclopropyl-8-fluoro-5-trifluoromethyl-1,4 -dihydro-4-oxo3-quinolinecarboxylic acid

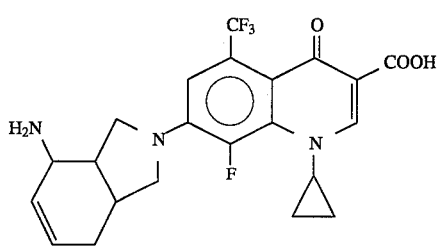

333 mg (1 mmol) of 1-cyclopropyl-7,8-difluoro-5-trifluoromethyl-1,4-dihydro-4-oxo-3-quinolinecarboxylic acid according to Example 12 are stirred overnight at room temperature with 165 mg (1.2 mmol) of 4-amino1,3,3a,4,7,7a-hexahydroisoindole and 224 mg (2 mmol) of 1,4-diazabicyclo[2.2.2]octane in 10 ml of dimethyl sulphoxide. All the volatile constituents are removed under a high vacuum and the residue is stirred with acetonitrile and dried at 100° C.

Yield: 330 mg (73% of theory) Melting point: 248°–249° C. (with decomposition)

EXAMPLE 14

7-(4-Amino-7-methyl-1,3,3a,4,7,7a-hexahydroisoindol-2-yl)- 1-cyclopropyl-8-fluoro-5-trifluoromethyl-1,4-dihydro4-oxo-3-quinolinecarboxylic acid

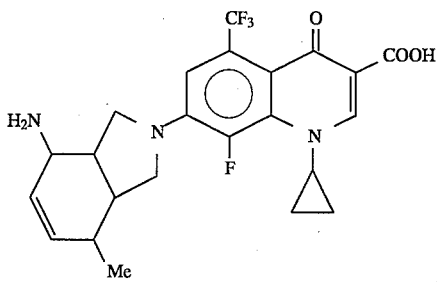

The title compound is obtained analogously to Example 13 by reaction of 1-cyclopropyl-7,8-difluoro-5-trifluoromethyl- 1,4-dihydro-4-oxo-3-quinolinecarboxylic acid with 4-amino-7-methyl-1,3,3a,4,7,7a-hexahydroisoindole.

Melting point: 242°–244° C. (with decomposition)

EXAMPLE 15

7-(4-Amino-1,3,3a,4,7,7a-hexahydroisoindol-2-yl)-1-cyclopropyl- 5-fluoro-8-trifluoromethyl-1,4-dihydro-4-oxo3-quinolinecarboxylic acid

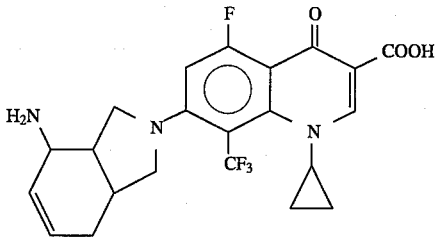

The title compound is obtained analogously to Example 13 by reaction of 1-cyclopropyl-5,7-difluoro-8-trifluoromethyl-1,4-dihydro-4-oxo-3-quinolinecarboxylic acid with 4-amino-7-methyl-1,3,3a,4,7,7a-hexahydroisoindole.

Melting point: 238°–240° C. (with decomposition)

EXAMPLE 16

7(4-Amino-7-methyl-1,3,3a,4,7,7a-hexahydroisoindol-2-yl)-1cyclopropyl-5-fluoro-8-trifluoromethyl-1,4dihydro-4-oxo-3-quinolinecarboxylic acid

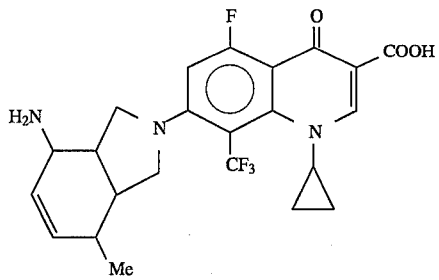

The title compound is obtained analogously to Example 13 by reaction of 1-cyclopropyl-5,7-difluoro-8-trifluoromethyl-methyl-1,4-dihydro-4-oxo-3-quinolinelinecarboxylic acid, obtained according to Example 11, with 4-amino-7-methyl-1,3,3a,4,7,7a-hexahydroisoindole.

Melting point: 234°–236° C. (with decomposition)

EXAMPLE 17

7-(4-Amino-7-methyl-1,3,3a,4,7,7a-hexahydroisoindol-2-yl)-1-cyclopropyl-8-trifluoromethyl-1,4-dihydro-4-oxo-3quinolinecarboxylic acid

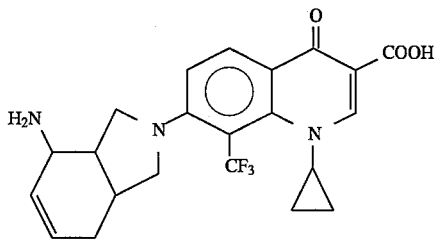

315 mg (1 mmol) of 1-cyclopropyl-7-fluoro-8-trifluoromethyl-1,4-dihydro- 4-oxo-3-quinolinecarboxylic acid according to Example 10 are stirred at 100° C. with 165 mg (1.2 mmol) of 4-amino-1,3,3a,4,7,7a-hexahydroisoindole and 224 mg (2 mmol) of 1,4-diazabicyclo[2.2.2]octane in 10 ml of dimethyl sulphoxide for two hours. All the volatile constituents are removed under a high vacuum and the residue is stirred witch acetonitrile and dried at 100° C.

Yield: 280 mg (65% of theory) Melting point: 168°–170° C. (with decomposition)

What is claimed is:

1. A Fluoro-trifluoromethylbenzoic acid derivative of the formula (I)

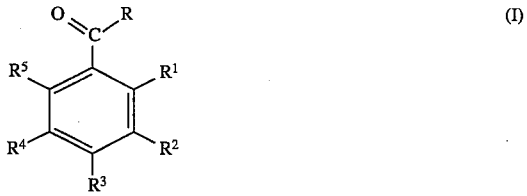

wherein

R represents hydroxyl, —OM, halogen or $C_1$–$C_4$-alkoxy, wherein

M represents an alkali metal and either a) $R^1$ represents F, $R^2$ represents F, $R^3$ represents H, $R^4$ represents H and $R^5$ represents $CF_3$ or b) $R^1$ represents F, $R^2$ represents $CF_3$, $R^3$ represents F, $R^4$ represents H and $R^5$ represents H or c) $R^1$ represents F, $R^2$ represents $CF_3$, $R^3$ represents H, $R^4$ represents H and $R^5$ represents F or d) $R^1$ represents F, $R^2$ represents F, $R^3$ represents $CF_3$, $R^4$ represents H a n d $R^5$ represents H or e) $R^1$ represents F, $R^2$ represents H, $R^3$ represents $CF_3$, $R^4$ represents H a n d $R^5$ represents F or f) $R^1$ represents F, $R^2$ represents F, $R^3$ represents F, $R^4$ represents H and $R^5$ represents $CF_3$ or g) $R^1$ represents F, $R^2$ represents $CF_3$, $R^3$ represents F, $R^4$ represents H $R^5$ represents F or h) $R^1$ represents F, $R^2$ represents F, $R^3$ represents H, $R^4$ represents $CF_3$ and $R^5$ represents F or i) $R^1$ represents F, $R^2$ represents F, $R^3$ represents F, $R^4$ represents $CF_3$ and $R^5$ represents H or k) $R^1$ represents F, $R^2$ represents F, $R^3$ represents $CF_3$, $R^4$ represents F a n d $R^5$ represents H or l) $R^1$ represents F, $R^2$ represents F, $R^3$ represents $CF_3$, $R^4$ represents H a n d $R^5$ represents F.

2. A Process for the preparation of the fluoro-trifluoromethylbenzoic acid derivative of claim 1 where R=hydroxyl in which a metallized fluoro-trifluoromethylbenzene derivative of the formula (II)

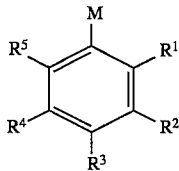

wherein

M represents an alkali metal and $R^1$, $R^2$, $R^3$, $R^4$ and $R^5$ have the meaning given in claim 1, is reacted with carbon dioxide, optionally in the presence of a diluent, at a temperature of −150° to 50° C. and subsequently the alkali metal carbonate of the formula (I) of claim 1 formed, where R=OM and M has the meaning given in claim 1, is reacted with an acid.

3. A Process for the preparation of a fluoro-trifluoromethylbenzonic acid derivative of claim 1, corresponding to the formula (I) wherein R represents hydrogen, in which a compound of the formula (I) of claim 1 where R=OH or OM and M has the meaning given in claim 1, is reacted with a halogenating agent, optionally in the presence of a diluent, at a temperature of 0° to 160° C.

4. A Process for the preparation of a fluoro-trifluoromethylbenzoic acid derivative of to claim 1, corresponding to the formula (I) where R=$C_1$-$C_4$-alkoxy, in which a compound of the formula (I) of claim 1 wherein R represents hydroxyl or halogen is reacted with an alcohol of the formula (III)

$$R^6-OH \qquad (III)$$

wherein $R^6$ represents $C_1$-$C_4$-alkyl, optionally in the presence of a diluent and in the presence of an acid-binding agent, at a temperature of 20° to 160° C.

5. The compound according to claim 1 wherein R is halogen.

6. The compound according to claim 1 wherein R is $C_1$-$C_4$-alkoxy.

* * * * *

UNITED STATES PATENT AND TRADEMARK OFFICE
CERTIFICATE OF CORRECTION

PATENT NO. : 5,493,048
DATED : February 20, 1996
INVENTOR(S) : Marhold, et al.

It is certified that error appears in the above-indentified patent and that said Letters Patent is hereby corrected as shown below:

Col. 18, line 25  After " and " insert -- optionally --

Signed and Sealed this

Thirteenth Day of August, 1996

Attest:

BRUCE LEHMAN

Attesting Officer         Commissioner of Patents and Trademarks